United States Patent
Lastovich et al.

(10) Patent No.: US 8,075,826 B2
(45) Date of Patent: Dec. 13, 2011

(54) MICROPROTRUSION ARRAYS AND METHODS FOR USING SAME TO DELIVER SUBSTANCES INTO TISSUE

(75) Inventors: Alexander G. Lastovich, Raleigh, NC (US); Jason B. Alarcon, Durham, NC (US); John P. Dekker, III, Cary, NC (US); M. Ishaq Haider, Morrisville, NC (US); John A. Mikszta, Durham, NC (US); Frank E. Martin, Durham, NC (US); Scott A. O'Connor, Durham, NC (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 358 days.

(21) Appl. No.: 12/487,374

(22) Filed: Jun. 18, 2009

(65) Prior Publication Data
US 2009/0270792 A1 Oct. 29, 2009

Related U.S. Application Data

(60) Division of application No. 11/942,138, filed on Nov. 19, 2007, now abandoned, which is a continuation of application No. 10/649,396, filed on Aug. 27, 2003, now Pat. No. 7,316,671.

(60) Provisional application No. 60/406,694, filed on Aug. 29, 2002.

(51) Int. Cl.
*B29C 59/02* (2006.01)
(52) U.S. Cl. ........................................ 264/322; 264/320
(58) Field of Classification Search .................. 264/320, 264/322
See application file for complete search history.

(56) References Cited

U.S. PATENT DOCUMENTS

| | | | |
|---|---|---|---|
| 2,688,970 A | | 9/1954 | Guye |
| 3,013,300 A | * | 12/1961 | Gaenzle ........................ 425/383 |
| 3,756,242 A | | 9/1973 | Coss |
| 3,918,449 A | | 11/1975 | Pistor |
| 3,964,482 A | | 6/1976 | Gerstel et al. |
| 5,003,987 A | | 4/1991 | Grinwald |
| 5,250,023 A | | 10/1993 | Lee et al. |
| 5,611,806 A | | 3/1997 | Jang |
| 5,618,295 A | | 4/1997 | Min |
| 5,679,647 A | | 10/1997 | Carson et al. |
| 5,843,114 A | | 12/1998 | Jang |
| 5,879,326 A | | 3/1999 | Godshall et al. |
| 5,964,729 A | | 10/1999 | Choi et al. |
| 5,983,136 A | | 11/1999 | Kamen |
| 6,050,988 A | | 4/2000 | Zuck |
| 6,083,196 A | | 7/2000 | Trautman et al. |
| 6,183,434 B1 | | 2/2001 | Eppstein |
| 6,230,051 B1 | | 5/2001 | Cormier et al. |
| 6,256,533 B1 | | 7/2001 | Yuzhakov et al. |
| 6,322,808 B1 | | 11/2001 | Trautman et al. |
| 6,334,856 B1 | | 1/2002 | Allen et al. |

(Continued)

FOREIGN PATENT DOCUMENTS

EP 0381410 8/1990

(Continued)

*Primary Examiner* — Christina Johnson
*Assistant Examiner* — Galen Hauth
(74) *Attorney, Agent, or Firm* — Robert E. West

(57) ABSTRACT

Improved microprotrusion abrasion devices having fluid retaining or directing patterns, and specific design parameters and method for delivery of substances into the skin. Various configurations of such devices are disclosed, including domed, channeled, patterned and stepped.

8 Claims, 9 Drawing Sheets

U.S. PATENT DOCUMENTS

| | | |
|---|---|---|
| 6,440,096 B1 | 8/2002 | Lostovich et al. |
| 6,503,231 B1 | 1/2003 | Prausnitz et al. |
| 6,537,242 B1 | 3/2003 | Palmer |
| 6,537,264 B1 | 3/2003 | Cormier et al. |
| 6,558,361 B1 | 5/2003 | Yeshurun |
| 6,562,014 B2 | 5/2003 | Lin et al. |
| 6,595,947 B1 | 7/2003 | Mikszta et al. |
| 6,835,184 B1 | 12/2004 | Sage et al. |
| 7,316,671 B2 | 1/2008 | Lastovich et al. |
| 2002/0010412 A1 | 1/2002 | Eppstein |
| 2002/0020688 A1 * | 2/2002 | Sherman et al. ............ 216/2 |
| 2002/0045859 A1 | 4/2002 | Gartstein et al. |
| 2002/0053756 A1 * | 5/2002 | Powell et al. ............ 264/313 |
| 2002/0077584 A1 | 6/2002 | Lin et al. |
| 2002/0091357 A1 | 7/2002 | Trautman et al. |
| 2004/0087992 A1 | 5/2004 | Gartstein et al. |

FOREIGN PATENT DOCUMENTS

| | | |
|---|---|---|
| EP | 1086719 A1 | 3/2001 |
| WO | WO 9512357 | 5/1995 |
| WO | WO 9617648 | 6/1996 |
| WO | WO 9748440 | 12/1997 |
| WO | WO 0202180 | 1/2002 |
| WO | WO 02032331 | 4/2002 |

\* cited by examiner

MICROPROTRUSION ARRAYS AND METHODS FOR USING SAME TO DELIVER SUBSTANCES INTO TISSUE

RELATED APPLICATIONS

This application is a divisional application of U.S. patent application Ser. No. 11/942,138, filed Nov. 19, 2007 now abandoned, which is a continuation of U.S. patent application Ser. No. 10/649,396, filed Aug. 27, 2003 now U.S. Pat. No. 7,316,671 which claims priority to U.S. Provisional Patent Application No. 60/406,694, filed Aug. 29, 2002, each of which is hereby incorporated by reference in their entirety. This application is also related to U.S. application Ser. No. 10/649,134; and U.S. application Ser. No. 10/649,395 both filed concurrently with application Ser. No. 10/649,396, each of which is hereby incorporated by reference in their entirety.

FIELD OF THE INVENTION

The present invention relates to devices and methods for abrading tissue such as the epidermis of animals and particularly of humans. More particularly, the invention is directed to arrays containing abrading microprotrusions and to methods for using such arrays to abrade the stratum corneum layer of human epidermis to thereby promote the intradermal delivery or sampling of a substance.

BACKGROUND OF THE INVENTION

Delivery of substances to the body through the skin has typically been invasive, involving needles and syringes to facilitate intradermal (ID), intramuscular (IM) or subcutaneous (SC) injection. These methods are painful for the subject, require the skills of a trained practitioner and often produce bleeding. There have been efforts to overcome these disadvantages by use of devices which abrade the stratum corneum, the thin external layer of keratinized cells about 10-20 μm thick. The bioactive substance is delivered to the exposed viable epidermis.

This technique avoids the nerve net and places the bioactive substance in close proximity to blood vessels and lymphatic system for absorption and delivery of the substance throughout the body.

For topical delivery of vaccines, the epidermis itself is a particularly desirable target as it is rich in antigen presenting cells. In comparison, the dermal layer below the epidermis contains fewer antigen presenting cells. Furthermore, the stratum corneum and epidermis do not contain nerves or blood vessels, so this method has the advantage of being essentially painless and blood-free while giving access to the skin layers capable of responding to the antigen.

The prior art reports a variety of devices and methods for disrupting the stratum corneum for the purpose of delivering substances to the body. For example, breach of the stratum corneum may be achieved by puncturing as taught in U.S. Pat. No. 5,679,647 to Carson, et al. This patent teaches that narrow diameter tines, such as those found on devices used for tuberculin skin tests and allergy tests, can be coated with polynucleotides or oligonucleotides and used for delivery of such materials into the skin. The method of using such devices involves puncturing the skin with the tines resulting in intracutaneous injection of the coated substance.

U.S. Pat. No. 5,003,987; U.S. Pat. No. 5,879,326; and U.S. Pat. No. 3,964,482 teach breaching the stratum corneum by cutting.

SUMMARY OF THE INVENTION

The present invention is directed to arrays containing abrading microprotrusions ("microarrays" or "microabraders") and methods for using such microarrays to abrade the epidermis animals, and particularly to abrade into the stratum corneum layer of human epidermis. The microarrays of this invention comprise a platen and microprotrusions spatial arranged into patterns, including random patterns on that platen. The shape of the platen onto or into which the microprotrusions are disposed, the shapes and dimensions of the individual microprotrusions, and the spatial arrangement of the microprotrusions are also encompassed by this invention.

One aspect of the invention is directed to a method and device for preparing a delivery site on the skin to enhance the delivery of a pharmaceutical agent through the stratum corneum of the skin to a sufficient depth where the pharmaceutical agent can be absorbed and utilized by the body. Such preparations are accomplished by the use of a device to impart a rotational movement to the entire microabrading device or the abrading microarray(s) of a microabrading device to disrupt the stratum corneum. Alternatively, a linear-type motion may be employed to disrupt the stratum corneum.

The present invention provides microprotrusions in arrays of random and patterned arrangements and methods to abrade the skin in conjunction with the delivery of one or more bioactive substances. Such bioactive substances include but are not limited to vaccines, pharmaceuticals, neurotransmitters, allergens, analgesics, nucleic acids, amino acids, amino acid derivatives, peptides or polypeptides. Numerous bioactive substances can be delivered by means of the present invention. For example, it has been discovered that nucleic acids exhibit enhanced gene expression and produce an enhanced immune response to the expressed protein when they are delivered simultaneously with abrasion of the stratum corneum. Similarly, allergens delivered simultaneously with abrasion produce a more vigorous immune response than conventional allergen testing methods. The bioactive substance can be delivered simultaneously with the abrading or immediately before the abrading, for example, by placing the bioactive substance on the target area of the epidermis prior to the abrading.

In general, a microarray according to the invention comprises a platen having at least one main surface. This surface is a microprotrusion surface having a plurality of microprotrusions optimally arranged thereon or therein, either randomly or in one or more patterns and arrangements, and adapted to abrade the stratum corneum while simultaneously retaining and delivering a liquid substance to the stratum corneum. Microprotrusions according to the invention can be of any design sufficient to abrade the desired or target tissue, but preferably have at least one scraping edge and can be formed by various methods recognized by those skilled in the art.

The platen may also contain a second main surface, an attachment surface, that is suitable for attaching the platen to a base or other surface, for example, a handle or device disposed or adapted to be grasped a user and used for applying the array to the skin to produce abrasion furrows therein. In a preferred method of use the microarray or a plurality of microarrays are rotated on the skin.

The platen further comprises a platen edge that is shaped or formed to have a desired surface shape so that it does not adversely affect the efficient use of the array during use. Preferable shapes for the edges in such embodiments of the invention include a bevel, radius or an arc connecting the microprotrusion surface to the attachment surface. In other embodiments where the stretching of skin in the target area is desired, the microarray can be provided with an abrupt edge so that the transition between the base and the microarray stretches the skin to a greater extent.

A plurality of microprotrusions, preferably comprising at least one scraping edge, are mounted in or otherwise disposed on or in the microprotrusion surface of the platen. The microprotrusions are spaced apart from one another and arranged randomly, or in patterns that, together with a predetermined fluid retaining spacing configured to maximize the efficiency of delivery of the desired substance into the stratum corneum or other layer by maintaining, or retaining, the substance within the target or abrasion site. The microarray is further adapted to present the abrading microprotrusions to the surface to be abraded in a manner that results in an efficient and uniform abrasion site, and, together with the fluid retaining spacing thereon or therein, minimize the displacement or dislocation of the substance to be delivered by helping to retain that substance within the confines of the microarray, or the abrasion site, when the microarray is applied to abrade the stratum corneum in a predetermined and proscribed manner.

The platen may also be domed in order to provide for an increased contact with the surface of the skin, as the abrader is pressed upon the skin. A domed platen, and therefore abrader, conforms to the dimple produced when the abrader pressed onto the skin. This domed abrader may provide for increased abrasion when utilized in a rotary or linear fashion.

It is therefore an object of the present invention to provide microprotrusion arrays suitable for disrupting tissue, such as epidermis, optimized to minimizes the displacement of a substance, such as vaccines and medicaments, from a site to be abraded.

It is a similar object of the present invention to provide microprotrusions of various shapes, lengths and widths and disposed into or on arrays in predetermined patterns such that they are adaptable in numerous combinations to minimizes the dislocation of one or more specific substances desired to be delivered at specific depths of target tissue and to retain the substance within the target area.

In accordance with these and other objects, the present invention provides microprotrusions in arrays for efficiently delivering a substance into tissue.

DETAILED DESCRIPTION OF THE INVENTION

Figure 1:
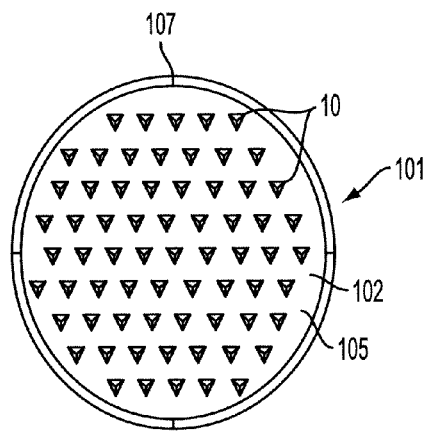
FIG. 1 is a top plan view of a circular microarray according to the invention.

Dermal tissue represents an attractive target site for delivery of vaccines and gene therapeutic agents. In the case of vaccines (both genetic and conventional), the skin is an attractive delivery site due to the high concentration of antigen presenting cells (APC) and APC precursors found within this tissue, especially the epidermal Langerhan's cells (LC). Several gene therapeutic agents are designed for the treatment of skin disorders, skin diseases and skin cancer. In such cases, direct delivery of the therapeutic agent to the affected skin tissue is desirable. In addition, skin cells are an attractive target for gene therapeutic agents, of which the encoded protein or proteins are active at sites distant from the skin. In such cases, skin cells (e.g., keratinocytes) can function as "bioreactors" producing a therapeutic protein which can be rapidly absorbed into the systemic circulation via the papillary dermis. In other cases, direct access of the vaccine or therapeutic agent to the systemic circulation is desirable for the treatment of disorders distant from the skin. In such cases, systemic distribution can be accomplished through the papillary dermis.

The primary barrier properties of the skin including the resistance to drug or vaccine delivery reside in the outermost layer of the epidermis, referred to as the stratum corneum. The inner layers of the epidermis generally include three layers, commonly identified as the stratum granulosum, the stratum malpighii, and the stratum germinativum. Once a drug or vaccine or other substance appears below the stratum corneum, there is essentially no resistance to diffusion into subsequent layers of the skin and eventual absorption by the body.

Delivering a substance into or through the viable epidermis can be an effective method for facilitating absorption of some substances, and particularly some vaccines, by the body. The present invention is primarily directed to a device and method for facilitating delivery of a substance, and particularly a pharmaceutical agent, into or through the viable epidermis so that more rapid absorption of larger quantities of the bioactive substance or pharmaceutical agent results.

As used herein, the term "abrade" refers to removing at least a portion of the stratum corneum to increase the permeability of the skin without causing excessive skin irritation or compromising the skin's barrier to infectious agents. This is in contrast to "puncturing" which produces discrete holes through the stratum corneum with areas of undisrupted stratum corneum between the holes.

As used herein, "penetrating" refers to entering the stratum corneum without passing completely through the stratum corneum and entering into the adjacent layers. This is not to say that that the stratum corneum can not be completely penetrated to reveal the interface of the underlying layer of the skin. Piercing, on the other hand, refers to passing through the stratum corneum completely and entering into the adjacent layers below the stratum corneum.

As used herein, "attached" or "attachment" refers to any means or method of affixing or otherwise causing one component to be non-releasably attached to another component. This attachment can even take the form of co-molding or otherwise co-forming of the individual components as a single or otherwise integral piece or compilation of pieces/components.

The microarrays of the present invention comprise microprotrusions, microprotrusion spacing and other fluid retaining or directing features configured specifically for abrading the stratum corneum in a rotary or circular fashion, as well as in abrasion in a linear fashion to enhance the administering of a substance through the stratum corneum of a patient.

The rotary method and the device for rotating a microabrader array surface according to the invention is capable of abrading the skin to increase the surface area within the epidermal layer and improve the efficacy of substance or drug or vaccine delivery into the body of the subject by either direct uptake by the antigen presenting cells (APC's), capillary drainage, or the lymphatic drainage phenomenon. In preferred embodiments, the device is capable of abrading the skin thereby penetrating the stratum corneum without piercing the stratum corneum.

Preferably, an abrading surface comprising a desired array of microprotrusions is rotated against a desired skin area. The resultant circular abrasion of the skin according to the invention disrupts the stratum corneum increasing the surface area of the viable epidermal layer, and minimizes the displacement or dislocation of the substance being delivered from the confines of the abrading surface or abrasion site so that a greatly increased dose concentration is achieved. The configuration of the microarray(s) of this invention, when used with a circular motion tend to keep the dose within the rotary or circular abraded area. Consequently, the dose can be limited to a smaller area by using the circular or spin delivery according to the invention resulting in increased substance delivered to a limited portion of the body, as the substance is not pushed away from the application site. For example, the substance can be contained in a 1 $cm^2$ circle, according to one embodiment of the invention. That is, the area abraded by using a substantially straight, back and forth technique can be about 2 times larger than an area abraded using the circular technique. Depending upon the subject or the substance being delivered, a smaller or larger abrading area may be used and delivered in a circular fashion and a smaller area will be abraded than with the same abrading surface when using a straight technique because the configuration of the microarray does not 'push' or dislocate the dose away from the abrasion site. Alternatively, multiple sites on the surface of the skin could be used, with a smaller abrasion area at each site.

In preferred embodiments the microarrays according to the invention, each array comprises a platen on or in which the microprotrusions are disposed or attached. Thus, the platen comprises a platen edge, and a microprotrusion surface suitable for mounting, molding, affixing, attaching, or otherwise retaining one or more microprotrusions thereon or therein. In another preferred embodiment, the platen may further comprise an attachment surface suitable for attaching the platen to a base or other surface, and connected to the microprotrusion surface by the platen edge.

The length and thickness of the microprotrusions are selected based on the particular substance being administered and the thickness of the stratum corneum in the location where the device is to be applied. Preferably, the microprotrusions penetrate the stratum corneum substantially without piercing or passing through the stratum corneum. The microprotrusions can have a length up to about 500 microns. Suitable microprotrusions have a length of about 5 to 500 microns. The microprotrusions in the illustrated embodiment have a generally pyramidal shape and are perpendicular to the plane of the device. These shapes have particular advantages in insuring that abrasion occurs to the desired depth. In preferred embodiments, the microprotrusions are solid members. In alternative embodiments, the microprotrusions can be hollow.

Microprotrusions 14 are may be spaced apart uniformly in rows and columns to form an array for contacting the skin and penetrating the stratum corneum during abrasion. Alternatively, a polar array of microprotrusions may be utilized. The spacing between the microprotrusions can be varied depending on the substance being administered either on the surface of the skin or within the tissue of the skin. Typically, the rows of microprotrusions are spaced to provide a density of about 2 to about 10 per millimeter (mm). Generally, the rows or columns are spaced apart a distance substantially equal to the spacing of the microprotrusions in the array to provide a microprotrusion density of about 4 to about 100 microprotrusions per mm2. In another embodiment, the microprotrusions may be arranged in a circular pattern. In yet another embodiment, the microprotrusions may be arranged in a random pattern. When arranged in columns and rows, the distance between the centers of the microprotrusions is preferably at least twice the length of the microprotrusions. In one embodiment, the distance between the centers of the microprotrusions is twice the length of the microprotrusions ±10 microns. Wider spacing is also included, up to 3, 4, 5 and greater multiples of the length of the microprotrusions. In addition, as noted above, the configuration of the microprotrusions can be such, that the height to the microprotrusions can be greater than the depth into the skin those protrusions will penetrate.

The platen of a microprotrusion array according to the invention may have a thickness measured between the attachment surface and the microprotrusion surface, or from the microprotrusion surface and the surface to which the platen is affixed, molded, or otherwise attached to, especially in an instance where that surface and the platen are integrally formed. The platen thickness can be uniform or non-uniform, as desired. For example, in some applications, the platen may be wedge-shaped in order to vary the pressure as the microprotrusion array is used to abrade the epidermis, or to fit into a complementary recess in a base. Alternatively, the platen may be stepped or consist of plateaus of varying heights and depths. Arrays according to the invention are useful for delivering one or more substances into tissue, such as the epidermis of an animal, and are especially useful for delivering one or more substances, such as vaccines, to the stratum corneum for absorption into the host.

The substance to be administered, using the methods of this invention, may be applied to the skin prior to abrading, or simultaneous with abrading. The substance may be delivered into the skin in any pharmaceutically acceptable form. In one embodiment, the substance is applied to the skin and an abrading device is then forced against the skin while being twisted or moved in a circular fashion over the skin and the substance. It is preferred that the minimum amount of downward force to produce the abrasion that achieves the desired result be used. The amount of force and rotation to achieve the necessary abrasion to achieve efficient delivery depends upon the drug or vaccine to be delivered. One of ordinary skill in the art would be able to determine the appropriate amount of force and rotation (and thus, the resultant abrasion) to achieve the appropriate amount of drug or vaccine delivery through routine experimentation.

In one embodiment, the substance may be applied in dry form to the abrading surface or an adjacent surface thereto or even contained within a storage reservoir of, or within the delivery device prior to application. In this embodiment, a reconstituting liquid can applied to the skin at the delivery site prior to or simultaneously with the application of the substance-coated abrading device. The abrading surface is then rotated against or rubbed in a circular fashion over the skin so that the substance concurrently or subsequently becomes dissolved in the reconstituting liquid on the surface of the skin and is delivered simultaneously with abrasion.

In one embodiment, the reconstituting liquid may be contained in or within the abrading device and released through openings in the platen to dissolve the substance as the device is applied to the skin for abrasion. Due to the containment of the liquid within a the abrading area when using a circular or linear abrading motion, the volume of reconstitution liquid may also be reduced, depending upon the needs of the substance to be applied.

According to the invention, skin disruption, for example, furrows or other openings will be formed in a circular fashion on the skin of a subject. If the microabrader abrading surface area is composed of a rectangular, square or other shaped arrays of microprotrusions that contain depressions or channels in the platens when the microabrader device is rotated or twisted, these channels help retain the reconstituting liquid, or active substance, within the abraded area and thus may minimize the amount of liquid lost due to the centrifugal force of the rotating microabrader abrading surface. In additional embodiments the channels may intersect or be in fluid communication with an abrader internal reservoir via passages in the platen so the liquid substance of diluent/reconstituting fluid will tend to remain in the abraded area. Thus, the circular abrasion method may possibly employ a lower volume of reconstitution liquid and suggests a reduction of substance loss since the abrader will form furrows that also capture the substance and possibly present an increase surface area for uptake of the substance, thereby avoiding the urging away of the substance as known in prior abrading methods.

The shapes of microprotrusion arrays according to the invention are determined by factors that optimize the efficiency and efficacy of delivery of the substance into the target tissue. These factors include the nature of the substance to be delivered, the nature of the tissue into which the substance is to be delivered, and the method of use to which the microarray will be subjected. For example, the elasticity and resistance to deformation of human skin are factors to be considered in choosing or adapting one of the many shapes contemplated by the present invention to a particular application. Another factor to be considered is that of the nature of the base upon which the array is to mounted, and how that base interacts with the target tissue. Most importantly, however, the direction of travel to which the microarray with be subjected will impact how well the microarray performs its tasks of abrading the skin and retaining the substance being administered at the abrasion site.

The overall shape of the platen, for example in plan view, and with respect to the platen edges can play an important role and is adaptable to numerous applications. For example, in some embodiments of microprotrusion arrays according to the invention, the platen edge has no corners. Examples of such cornerless platen edges include circles, ellipsoids such as those having two foci, kidney shapes, freeform curves and other curves. The platen edge can be smooth, beveled, ridged, dentate, or roughened, for example, to adapt it for attachment with an adhesive. In plan view, platens of the invention can also be polygons such as squares, triangles, tetragons, pentagons, hexagons, heptagons, nonagons, decagons, or any other regular or irregular polygon shape.

In accordance with other aspects of microprotrusion arrays according to the invention, the attachment surface comprises attachment means for attaching the array to a base. A base for use with the present microprotrusion arrays is constructed and arranged to engage the corresponding attachment means on the attachment surface of the microarray. Suitable attachment means include one or more of adhesives, heatstakes, heat seal tabs, splines, teeth, slots, slits, grids, tabs, pins, dowels, ribs, lugs, flanges, notches, snaps, threads, and at least one of hooks and loops from hook and loop fastener pairs. In some preferred embodiments, the attachment surface of an array can also include alignment means for providing alignment of the array with respect to a base and with respect to a base constructed and arranged to engage the alignment means.

Alignment means include, for example, heatstakes, heat seal tabs, splines, teeth, slots, slits, grids, tabs, pins, dowels, ribs, lugs, flanges, notches, snaps, and at least one of hooks and loops from hook and loop fastener pairs. In accordance with additional aspects of the invention the alignment means may comprise the attachment means. For example, a heatstake disposed upon the attachment surface of a microprotrusion array can be constructed and arranged to fit in only one disposition on a corresponding base such that the array can be mounted only in a desired alignment with respect to the base.

The platen may also be integrally formed with that other surface or device, such as by molding, over-molding, stamping or as is otherwise recognized in this art. In these instances the distance from the base surface and the platen microprotrusion surface is the platen thickness and this thickness constitutes the platen edge.

Microprotrusion arrays according to the present invention can be produced such that the microprotrusion surface of the platen is of any desired shape, but configured to minimize the displacement or dislocation of the applied liquid substance when the array is used to abraded in a circular or rotational manner. For example, the microprotrusion surface of the platen can be substantially planar, concave, convex, cylindrical or in other arcuate shapes. Similarly, the attachment surface of the platen can be of any desired shape such as substantially planar, concave, convex, cylindrical or arcuate. Examples of arcuate platens include those where the microprotrusion array surface approximates at least a portion of a parabola, a sphere, a cylinder or an ellipsoid.

In most preferred embodiments of the invention where the microprotrusion surface of the platen is substantially planar, the attachment surface of the platen is also planar and is disposed substantially parallel to the microprotrusion surface. In other embodiments where both the microarray and attachment surfaces are substantially planar, the attachment surface can be disposed non-parallel to the microprotrusion surface to thereby form a wedge-shaped platen. Wedge shaped platens, or abrader device surfaces to or which the platen is disposed are one of the preferred configurations for use in rotary abrading applications.

Arcuate shapes of platens according to the invention include those that are substantially lenticular, that is, the shape of the platen approximates the shape of one of several types of optical lenses. One example of a lenticular shape according to the invention is plano-convex with the attachment surface of the platen being substantially planar and the array surface being convex. Other examples of lenticular shapes include that of a converging meniscus, where the arcs of the attachment and array surfaces intersect, thus forming a sharp edge, and that of a diverging meniscus where the arcs of the attachment and array surfaces do not intersect. In a diverging meniscus lenticular shape, the distance between the respective arcs at the edge of the platen increases as one measures farther from its center. Another arcuate shape according to the present invention is a cylindrical bend, in that an arcuate shape of the platen is made, as if it were formed around a cylinder, and arced about only a single axis.

In accordance with other preferred embodiments, the microprotrusion surface may comprise one or more channels disposed between the microprotrusion bases. The microprotrusion surface can also comprises a plurality of continuous or discontinuous channels between the microprotrusion bases, the channels being disposed in one direction or in more than one direction and thus can be non-intersecting or intersecting as desired. In other preferred embodiments, the microprotrusion surface comprises at least one recess disposed between the microprotrusion bases. The recess or recesses can be constructed and arranged for receiving or storing a material such as an active substance, adjuvants, carriers, diluents, or a solvent of the substance or of a carrier as the microarray is rotated on the skin of an individual recipient.

In other embodiments the microprotrusion surface of the platen may contain areas thereon or therein that are devoid of microprotrusions or where the density, i.e., number of microprotrusions per area, is less than an adjacent area. The microprotrusion-free or reduced-density area serving to retain or direct the majority of the liquid substance to be delivered into or within the abrasion area or site, or preferably, within the confines of the microarray itself.

Platens with microprotrusions according to the invention are provided with microprotrusions of sufficient length, appropriate shape and specifically spaced apart to deliver an active substance, such as a vaccine, into the target tissue and actively retain or confine the majority of that substance within the target site.

A platen according to the invention comprises at least one microprotrusion. In some preferred embodiments of the invention the platen comprises dozens or hundreds of microprotrusions. These microprotrusions may also be disposed on the platen in specific and varying patterns, including patterns with areas devoid of microprotrusions or areas have higher and lower densities of microprotrusions. In a preferable description, each of the microprotrusions comprises: i) a microprotrusion base having a base center and a base circumference, ii) a microprotrusion tip, and iii) a longitudinal axis having a microprotrusion length from the base center to the microprotrusion tip. In some preferred embodiments, the base circumference comprises a base margin and the base margin comprises an edge, the edge having an edge length.

In some preferred embodiments, some or all of the longitudinal axes of the microprotrusions are disposed substantially normal to the microprotrusion surface of the platen. In other embodiments, some or all of the microprotrusion longitudinal axes are disposed substantially non-normal to the microprotrusion surface of the platen. Thus, the microprotrusions according to the invention can be disposed in various ways with respect to the surface of the platen.

In preferred embodiments, the lengths of the microprotrusions are greater than the depth to which they are intended to penetrate into the stratum corneum layer of the epidermis. In such embodiments where the lengths of the microprotrusions are greater than the depth to which they are intended to penetrate, one means of depth control is the shape of the microprotrusion themselves, and the density at which the microprotrusions are provided on the platen. Thus, depending upon the target tissue upon which the microarray will be used, the desired microprotrusions are shaped and dispersed at such a density that the pressure to be applied to the microarray causes the tips of the microprotrusion to penetrate into the stratum corneum and no further even though the length of the microprotrusions is longer than the depth of the stratum corneum. For example, with frustoconical microprotrusions having bases broad in comparison with their heights, the rapidly increasing angle of incidence of the microprotrusion arc facets with the target tissue prevents the microprotrusions from penetrating to their full depth because of the rapidly increasing pressure produced by the diverging sides of the frustocone.

The present invention provides for many permutations of microprotrusion lengths. In some embodiments of the invention, the microprotrusion lengths are substantially equal to one another. In other embodiments, they are unequal to one another. Thus, depending upon the desired use and penetration depth, microarrays of the invention can be manufactured in dimensions appropriate for a specific use. For example, microprotrusion lengths can be made to vary from the platen edge to the center of the microprotrusion array such that the lengths increase from the platen edge to the array center whereby the microprotrusion tips approximately a desired shape, for example, a portion of a sphere, cylinder or ellipsoid. In other applications, it may be desirable for the lengths to decrease from the platen edge to the array center, for example, where the platen itself is domed and the relative lengths of the microprotrusions are such that the degree of doming of the microprotrusion tips is less than that of the platen.

The microprotrusions of the invention are provided in lengths suitable for their intended uses. For example, for use in penetrating in to the stratum corneum of a human epidermis, they are preferably in a range from 5 to 500 microns. More preferably the microprotrusion lengths are in a range from 50 to 300 microns, or from 140 to 250 microns, and most preferably from 160 to 220 microns.

In accordance with still additional aspects of the invention, the shape of the microprotrusions and their relationship to the platen can be adjusted such that the depth of penetration of the microprotrusion into the tissue is controlled. For example, the microprotrusions are constructed and arranged on or in the microprotrusion surface of the platen such that the microprotrusion length does not determine the depth of penetration of a plurality of the microprotrusions into the tissue. Conversely, the microprotrusions can be constructed and arranged on or in the microprotrusion surface of the platen such that the microprotrusion length determines the depth of penetration of the plurality of microprotrusions into the tissue.

Thus, by controlling the length, shape, number of scraping edges, and density of the microprotrusion, the depth of penetration, degree of disruption of the tissue and the liquid retention capacity can be accomplished to a desired extent for delivery of substance into the target tissue. Microprotrusions of the invention can be arranged randomly or in a pattern, of a single length or of multiple lengths. In embodiments utilizing a patterned array of microprotrusions, the platen, microprotrusions, or both can be arranged or disposed to form a one directional symbol or design suitable for orienting the array with respect to the tissue. Examples of such symbols and designs can include, for example, arrows, triangles, V-shaped patterns, stars, airplane propeller and other symbols arranged in a directional manner or disposed on or near an edge of the platen to thereby indicate either the proper position of the microprotrusion array upon the base, or the direction or directions in which the device should be moved in relation to the tissue.

Thus, microprotrusions of the invention can be of substantially equal or unequal lengths, depending upon the specific application of the device. Variations in the edge of the platen are also within the scope of the invention. The edge of the platen can be smooth, such as in an arc, or cylindrical as forming a surface that is perpendicular to a planar base at all points, or sharpened such as that formed by a converging meniscus in a lenticular platen.

Microprotrusions can be made from a plastic material that is non-reactive with the substance being administered. A non-inclusive list of suitable plastic materials include, for example, polyethylene, polypropylene, Poly methyl methacrylate (PMMA), polyamides, polystyrenes, polyesters, and polycarbonates as known in the art. Alternatively, the microprotrusions can be made from a metal such as stainless steel, tungsten steel, alloys of nickel, molybdenum, chromium, cobalt, titanium, and alloys thereof, or other materials such as silicon, ceramics and glass polymers. Metal microprotrusions can be manufactured using various techniques similar to photolithographic etching of a silicon wafer or micromachining using a diamond tipped mill as known in the art. The microprotrusions can also be manufactured by photolithographic etching of a silicon wafer using standard techniques as are known in the art. They can also be manufactured in plastic via an injection molding process, as described for example in U.S. application Ser. No. 10/193,317, filed Jul. 12, 2002, which is hereby incorporated by reference. Those skilled in the art will recognize other, alternative ways to make microprotrusions If desired for a particular application, the substance to be delivered can be provided upon some or all of the microprotrusions in any form suitable for delivery into the target tissue. For example, the substance may be provided in the form of dried or partially dried coatings, liquids, gels, powders, beads, or emulsions.

The present invention also provides for non-circular patterns of microprotrusions. For example, patterns according to the invention include those comprising rows of microprotrusions, each row having an axis. Microprotrusions can be offset from one another with respect to the several rows. The microprotrusions in each respective row can be oriented the same way with respect to the row axis, or oriented in different ways.

Microprotrusion arrays according to the present invention can further comprise a perforation through the platen from the attachment surface to the microarray surface. The perforation can be disposed anywhere in the platen, for example in the center of the platen near the edge of a platen or anywhere in between. The perforation can be of any desired dimension sufficient to accomplish delivery of the substance in proximity to or on to the microprotrusion surface of the platen. In some embodiments, the platen comprises a plurality of perforations that may be disposed between or through the microprotrusions. In such embodiments, the plurality of perforations can be disposed randomly or in a pattern such as one arranged to correspond to one or more voids disposed on or in the base. In other embodiments, the plurality of perforations can be disposed to communicate with channels disposed in the platen, or with recesses disposed in the platen. In yet other embodiments, the plurality of perforations can be disposed near the edge of the platen.

Microprotrusions of the invention can be provided in any shape suitable for effective delivery of the substance in the target tissue. In one particular preferred embodiment, the microprotrusions are frustocones, each comprising arc facets extending from the base of the microprotrusion to the tip of the microprotrusion. Preferably, each of the frustoconical microprotrusions of the present invention comprises three or more arc facets. More preferably, each frustoconical microprotrusion comprises between three and six arc facets wherein the intersection of any two of the arc facets forms a scraping edge such that each frustocone comprises at least one scraping edge. In some preferred embodiments of the invention, at least some of the arc facets comprise a textured surface such as the grooves or bumps that would be formed by chemical etching or molding. In the case of grooves formed into the arc facet, they can be disposed substantially parallel to the microprotrusion surface of the platen or at non-parallel angles. Moreover, the grooves or texture formed into such arc facets can be constructed and arranged for receiving and holding a material such as the substance to be delivered, a diluent, or a component of the substance or the like.

The axis of each microprotrusion is disposed from the center of its respective base through the center of its respective tip. Microprotrusions of the invention can have a relatively broad or relatively narrow base when compared with the microprotrusion length. Thus, the distance between the respective tips of the microprotrusions can be used to describe the relative density of the tips. For example, when the microprotrusions are disposed in a grid, such as a square grid where four microprotrusion tips form the four corners of a square, the distance between the respective tips can be used as a density indicator. In one preferred embodiment of a microarray grid according to the invention, the distance between the tips of the microprotrusions is preferably in a range from 100-850 microns or preferably in a range from 180-500 microns or, more preferably in a range to 380-450 microns. As with other embodiments, the patterns contemplated by the invention can be disposed on planar or curved surfaces, and may comprise microprotrusions of different lengths.

Microprotrusions use with the invention may be formed to comprise a flat tip. For example, a flat tip can be the result of acid etching, or of post-molding flattening or other ways known to those skilled in the art. The flat tip can be disposed substantially perpendicular to the longitudinal axis of the microprotrusion or can be disposed at an acute angle to the longitudinal axis. In some embodiments of the invention, the flat tip comprises a mesa structure formed at the intersection between the arc facets and the flat tip. The mesa facet can be disposed substantially perpendicular or at an acute angle to the longitudinal axis of the microprotrusion. Moreover, the mesa structure can comprise at least one scraping edge, for example, formed by the intersection of an arc facet and the flat tip mesa, or a scraping rim formed by the intersection of one or more arc facets and the flat facet of the mesa structure. Preferably, the intersection of any two facets, such as an arc facet and a mesa facet forms a scraping edge on the microprotrusion.

In accordance with other advantageous characteristics of the present invention, the microprotrusions can have shapes other than frustocones. For example, the microprotrusions can comprise circular cones, such as right circular cones having central axis wherein each axis is disposed substantially normal to the attachment facet of the plate. Such circular conical microprotrusions may comprise a flat tip and the flat tip may be disposed substantially perpendicular to the longitudinal axis of the microprotrusion or at an acute angle to that axis. The flat tip of the circular conical microprotrusion can comprise a mesa structure having a substantially planar mesa facet. Preferably, the mesa facet is disposed substantially perpendicular to the longitudinal axis of the microprotrusion or at an acute angle to the longitudinal axis of the microprotrusion. Preferably, the mesa structure comprises at least one scraping edge or scraping rim formed by the intersection of the mesa facet and at least one surface of the shaft of the microprotrusion.

As a further advantage, the present invention provides methods for using the microprotrusion arrays of the invention to deliver one or more substances to a desired depth in a target tissue, for example, to deliver a vaccine, allergen or immunogen to the stratum corneum of human skin. In one preferred embodiment, a method according to the invention comprises the steps of I) providing a microprotrusion array, the array comprising a platen, the platen comprising a microprotrusion surface suitable for mounting a plurality of microprotrusions thereon or therein, a platen edge connecting the microprotrusion surface to an attachment surface or the surface of an abrader base, a spacing of channel located between two or more microprotrusions; and a plurality of microprotrusions mounted in or on the microprotrusion surface of the platen, wherein each of the microprotrusions comprises at least one scraping edge, and II) moving the microprotrusion array in a circular motion on or across the surface of the tissue to provide abrasions therein.

The present methods include a variation whereby the substance or substances to be delivered are provided on at least some of the microprotrusions, on spaces or voids between the bases of the microprotrusions such as grooves or channels. In other preferred embodiments of the present methods, the microprotrusion array is attached to a base or handle so that it can be used to abrade skin or other tissue more efficiently.

Exemplary embodiments of the invention will now be described with reference to the FIGS. 1-8. As is disclosed herein, the permutations of the platens, microprotrusions and patterns of the present invention are too numerous to illustrate herein. Nonetheless, as one of skill in the art will comprehend from the present disclosure, the many variations of microabraders of the invention can be practiced with reference to the present specification without undue experimentation.

With reference to FIG. 1, microprotrusion array 101 includes substantially planar platen 102 having platen edge 107 with a plurality of triangular frustoconical microprotrusions 10 disposed thereon. Microprotrusions 10 are aligned in parallel rows and are each oriented such that the respective base edges of microprotrusions 10 approximate a straight line. Triangular frustoconical microprotrusions 10 are attached to microprotrusion attachment surface 105 of platen 102 by adhesive, heat welding, electron beam welding, or may be co-molded or otherwise made integral with platen 102 as will be recognized by one skilled in this art. Alternatively, the frustoconical microprotrusions may be produced with a lithography-type process. Typically, a platen such as platen according to the invention has a surface area of about 1 to about 4 cm². The present invention is not limited to Triangular frustoconical microprotrusions 10, which terminate in a small mesa, and could be applied to microprotrusions of the pointed-type as well. Further designs of the mesa-type are described in U.S. Pat. No. 6,331,266, which is herein incorporated by reference.

Figure 2:
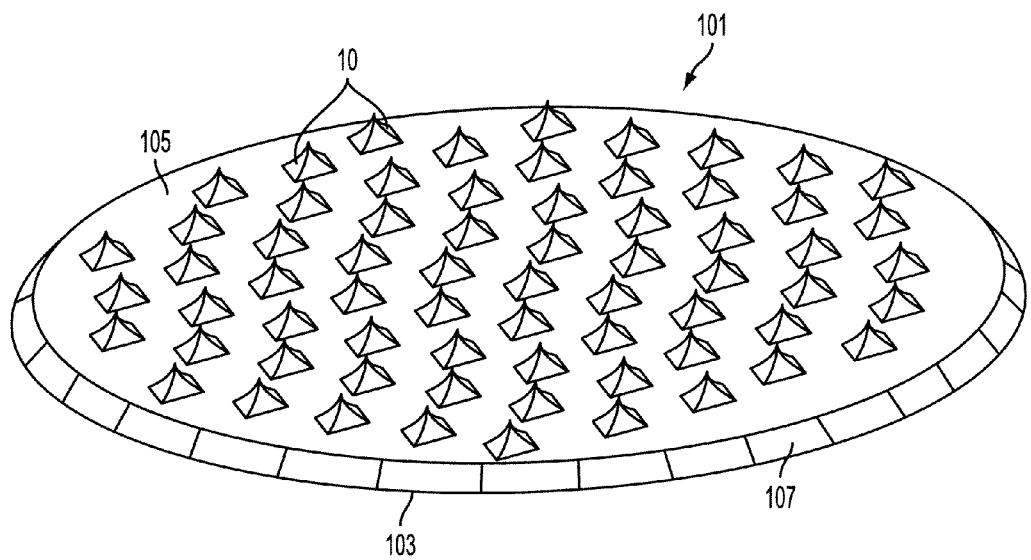
FIG. 2 is a perspective view of a microprotrusion array similar to that shown in FIG. 1.
Figure 3:
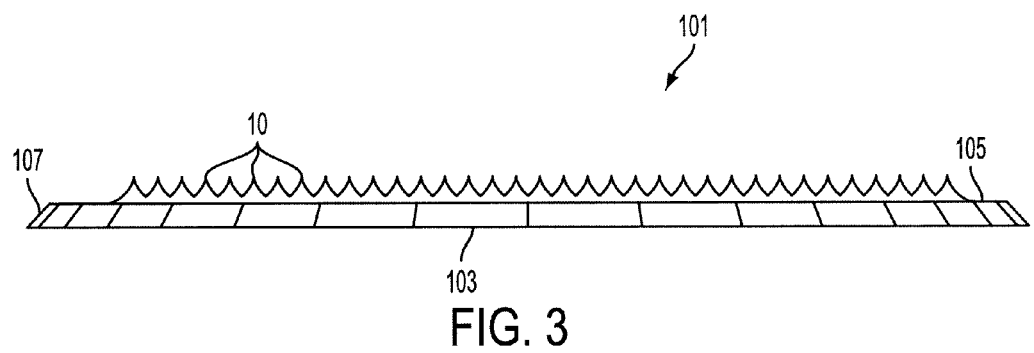
FIG. 3 is an edge view of the array shown in FIG. 2.

FIG. 2 is a perspective view of the microprotrusion array shown in FIG. 1, showing beveled, platen edge 107 connecting substantially planar attachment surface 103 with substantially planar microprotrusion surface 105 having a multiplicity of triangular frustoconical microprotrusions 10 disposed thereon or therein. FIG. 3 is an edge view of the microprotrusion array shown in FIGS. 1 and 2 and shows substantially planar attachment surface 103 connected to substantially planar microprotrusion attachment surface 105 by beveled platen edge 107. FIG. 3 also shows a multiplicity of triangular frustoconical microprotrusions 10 and their relative spacing from one another.

Figure 4:
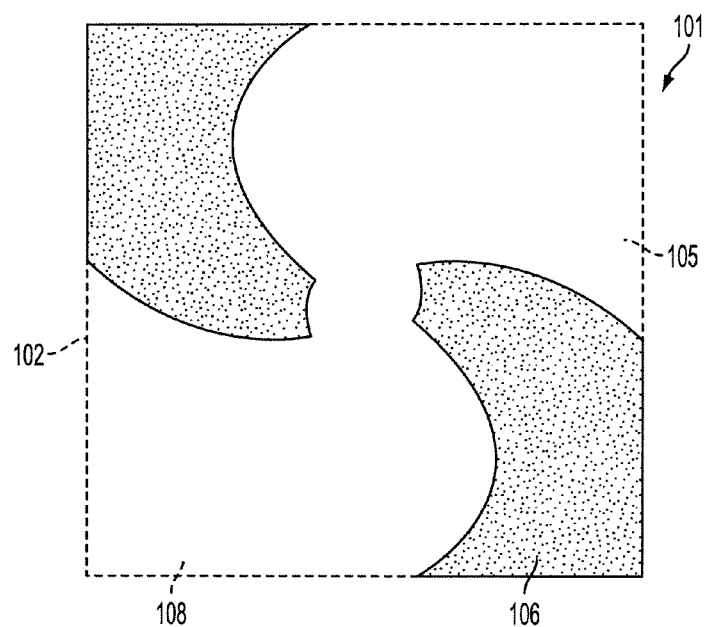
FIG. 4 is a top plan view of one embodiment of a microarray of the invention configured for rotational application.

FIG. 4, shows an essentially square or rectangular microprotrusion microarray 101 configured for use with a circular or rotational application and includes platen 102. The platen 102 and microprotrusion attachment surface 105 of this embodiment comprises areas containing microprotrusions 106 as well as areas devoid of any microprotrusions 108. Areas 106 and 108 may constitute larger or smaller proportions of platen 102 than depicted in FIG. 4 and still be within the scope of this invention. As will be noted, the combination of microprotrusion-free and microprotrusion-containing areas 106 and 108 gives microarray 102 the appearance of a two-bladed propeller. Other, multi-blade designs can also be configured and still be within the scope of this invention, i.e., numerous microprotrusion-containing and microprotrusion-free areas (or areas of reduced microprotrusion density).

Figure 5:
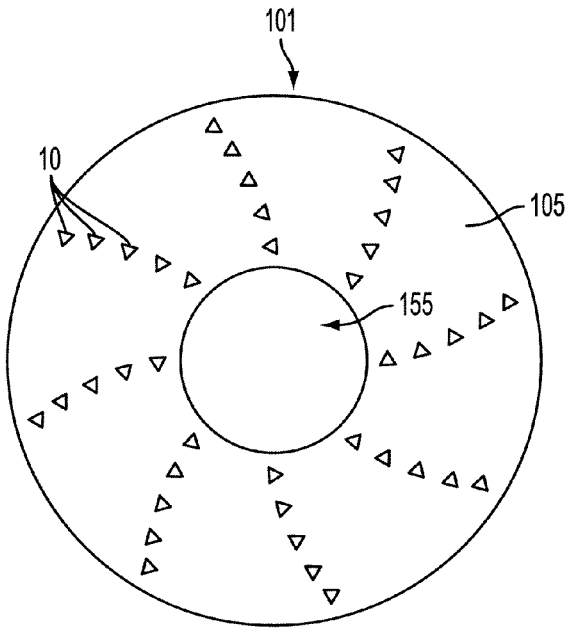
FIG. 5 is top plan view of another embodiment of a microarray for circular or rotational application.

FIG. 5, shows an alternate embodiment of and array 101. The shape of the array shown is a circle but may have any shape desired for the particular application. area 155 is devoid of microprotrusions 10 and can be merely devoid of microprotrusions, of devoid and recessed as well, serving as a supply reservoir for the liquid substance to be applied during abrasion. Area 155 may also contain a fluid passageway (not shown) to an underlying substance supply reservoir (not shown) for supplying the active substance during or before abrasion.

Figure 6:
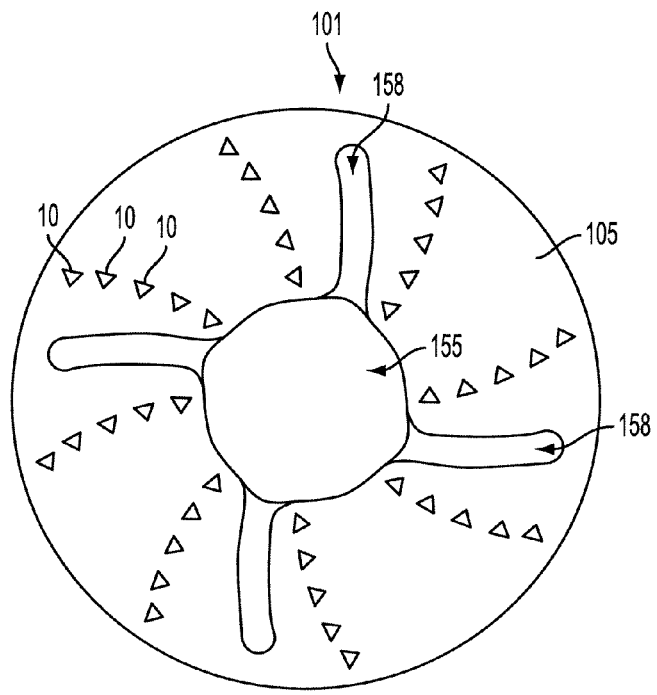
FIG. 6 is a top plan view of another embodiment of the array shown FIG. 5 having channels added thereto.

FIG. 6 shows a further modified embodiment of the array of FIG. 5. The array of FIG. 6 contains the reservoir area 155 of FIG. 5 but also channels 158 which serve to retain and direct the fluid substance to retain the substance within the confines of the array with minimal fluid displacement.

The disposition of the microprotrusions 10 in FIGS. 5 and 6 are arcuate and also configured to assist in retaining the liquid substance to be administered within the abrasion site, or most preferably, within the confines of the array itself.

Figure 7:
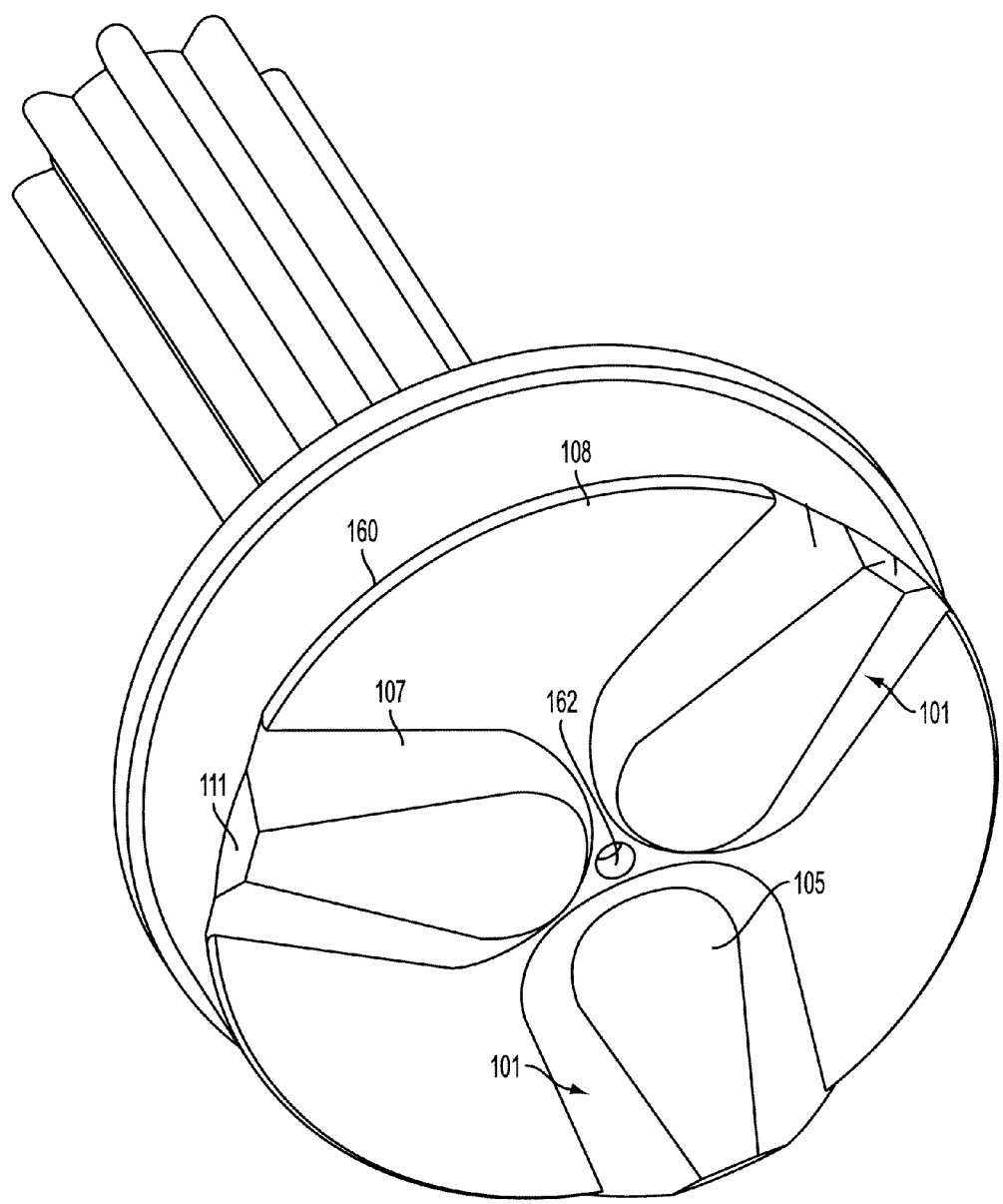
FIG. 7 is a perspective view of a preferred embodiment of a microarray comprising microprotrusion-free areas and raised microprotrusion-containing surfaces.

FIG. 7 shows a preferred embodiment of the microarrays with the platen attached or integrally formed on an underlying base of an abrading device disclosed and claimed in co-pending application Ser. No. 10/649,134, filed concurrently herewith, the contents of which previously were incorporated by reference. In this embodiment the platen edge 107 is beveled and an angle of from about 20° to about 70° more preferably about 30° to 60° and comprises the distance from the microprotrusion surface 105 to the base 160. Microprotrusion surface 105 comprises a bed of individual abrading microprotrusions 10 (not shown in FIG. 8) with a spacing between the microprotrusions of from about 200µ to about 800µ, which translates to a density of approximately 400 microprotrusions per cm². Microprotrusion surface 105 also has a reverse taper, which provides for an equal swept area at every radius. If the microprotrusion surface became wider or was of uniform width as the radius increased, the outer edge of the circular abraded area would be abraded significantly more than the area closer to the rotational axis. Platen 102 also comprises and additional beveled edge 111. Microprotrusion-free space 108, serves as a reservoir in this embodiment. Fluid substance dispensing port 162 supplies the substance to be administered from an internal fluid storage reservoir (not shown) in this embodiment.

The microprotrusion-free areas 108 in conjunction with the platen edge 107 and the shape and configuration of the microarray will tend to pull and direct the liquid substance toward the center of the array, counteracting the centrifugal forces generated during rotation.

Figure 8:
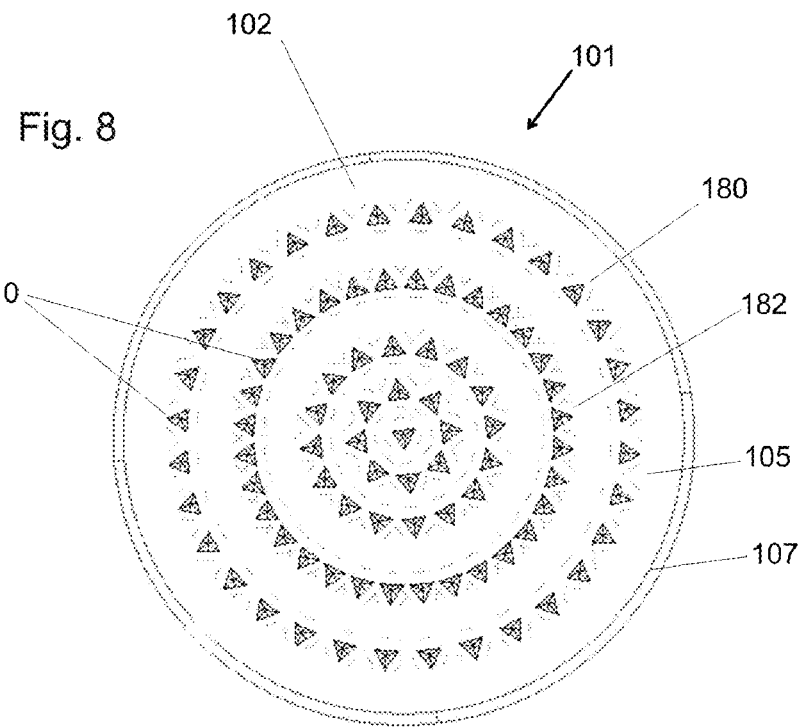
FIG. 8 is a top plan view of another embodiment of a microarray.

FIG. 8 shows an alternate embodiment of the invention, which is similar to that of FIG. 1, however, the difference of the embodiment of FIG. 8 and the embodiment of FIG. 1 is that this embodiment utilizes a polar array of microprotrusions 10, and optionally has a different design of the radially outermost ring 180. This embodiment of the invention utilizes a reduced microprotrusion 10 count on outermost ring 180 with substantially the same number of microprotrusions in outermost ring 180 as the preceding ring 182, in this case, the radial third row from the center. Effectively, this design increases the spacing between microprotrusions 10 on outermost ring 180. Alternatively, the microprotrusion center of the array could be replaced with a drug effluent port, which would be in fluid communication to a drug reservoir.

Figure 9:
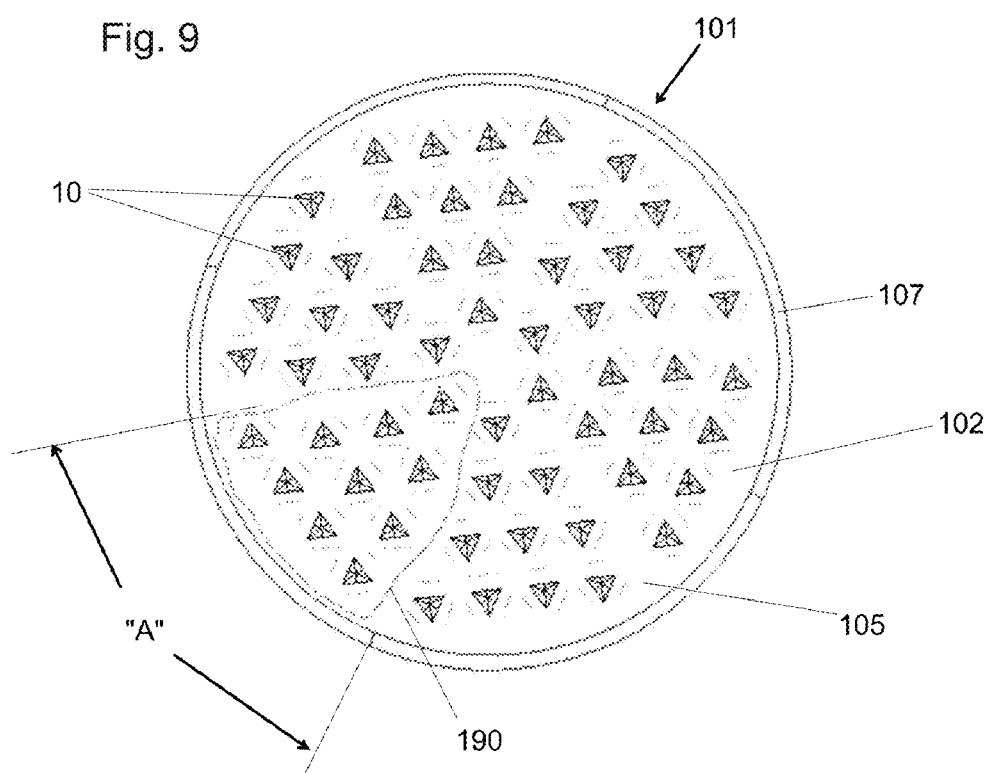
FIG. 9 is a top plan view of another embodiment of a microarray.

FIG. 9 shows an alternate embodiment of the present invention, which, is based on a similar platen 102 design of the previous embodiments. The difference from the embodiment of FIG. 1 is in the microprotrusion 10 pattern, which in this embodiment is repeat pattern design of a polar nature. Shown in the figure is block 190, which is a grouping of microprotrusions 10 which is then copied and rotated about the radial center of platen 102. Block 190 has an approximate 60° angle with its apex at the radial center of platen 102. To form a full pattern of microprotrusions across the surface of platen 102, block 190 is rotated and copied 6 times to form a 360° pattern as shown. One of the advantages of such a design is that the angle "A" may be chosen in such a fashion that a channel may be formed between adjacent blocks 190. For example, if a block of microprotrusions were created with an "A" angle of only an 86°, yet were to be rotated and copied 4 times about 360°, there would be a 4° microchannel between adjacent blocks. These microchannels would be utilized to direct the fluid, which is in fluid communication with an abrader internal reservoir via passages in the platen so the liquid substance of diluent/reconstituting fluid will tend to remain in the abraded area. In a second example, a block angle "A" of 180° may be utilized, and the microprotrusions may be spaced distant from a diameter (or chord) of the circular platen. When this is copied and rotated for a total of 2 copies, a single strip microchannel is formed across a diameter of the platen. This microchannel may be utilized for drug delivery or alternatively, could be utilized as a directional assembly feature for assembly of the platen to a handle.

Figure 10:
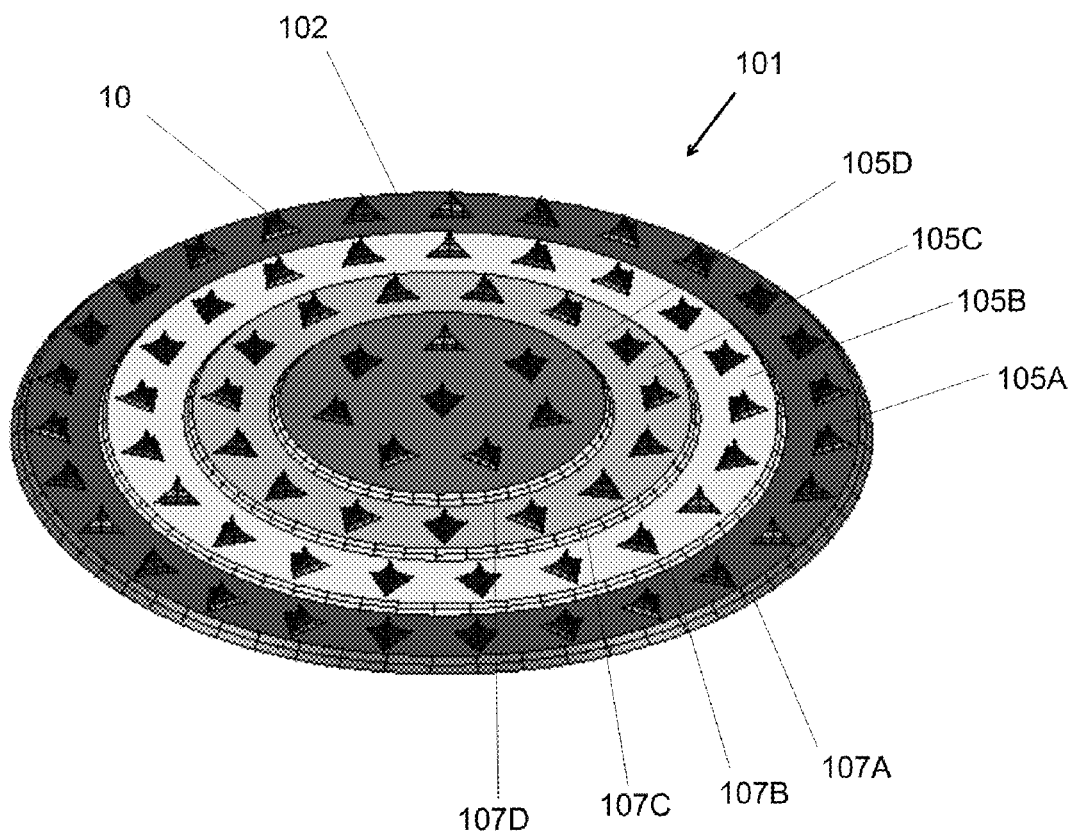
FIG. 10 is a top plan view of another embodiment of a microarray.

FIG. 10 shows another embodiment of the present invention in which the platen surface 105 is a multitude of platen surfaces 105A.105D of variable height. As shown in the figure, Platen 105B is of a greater height than that of platen surface 105A, however, this is not required and the opposite could be true, in that the height of platen surface 105B could be less than that of platen surface 105A. In this figure, a total of four platen surfaces are shown, however, more or less platen surfaces may be utilized in the invention, depending on the desired abrasion effect. Platen surfaces are interconnected by a multitude of edges, shown as 107A.107D. The difference in height between each of the platen surfaces 105A.105n.s between 5 and 1000 μm, preferably between 25 μm and 500 μm, and more preferably between 75 μm and 200 μm. Patterns of microprotrusions 10 may be of any of the design layouts discussed in this application, however it is preferred to utilize polar-type designs, and are utilized across the various platen surfaces 105A.n to best accomplish the abrasion and drug delivery process.

Figure 11:
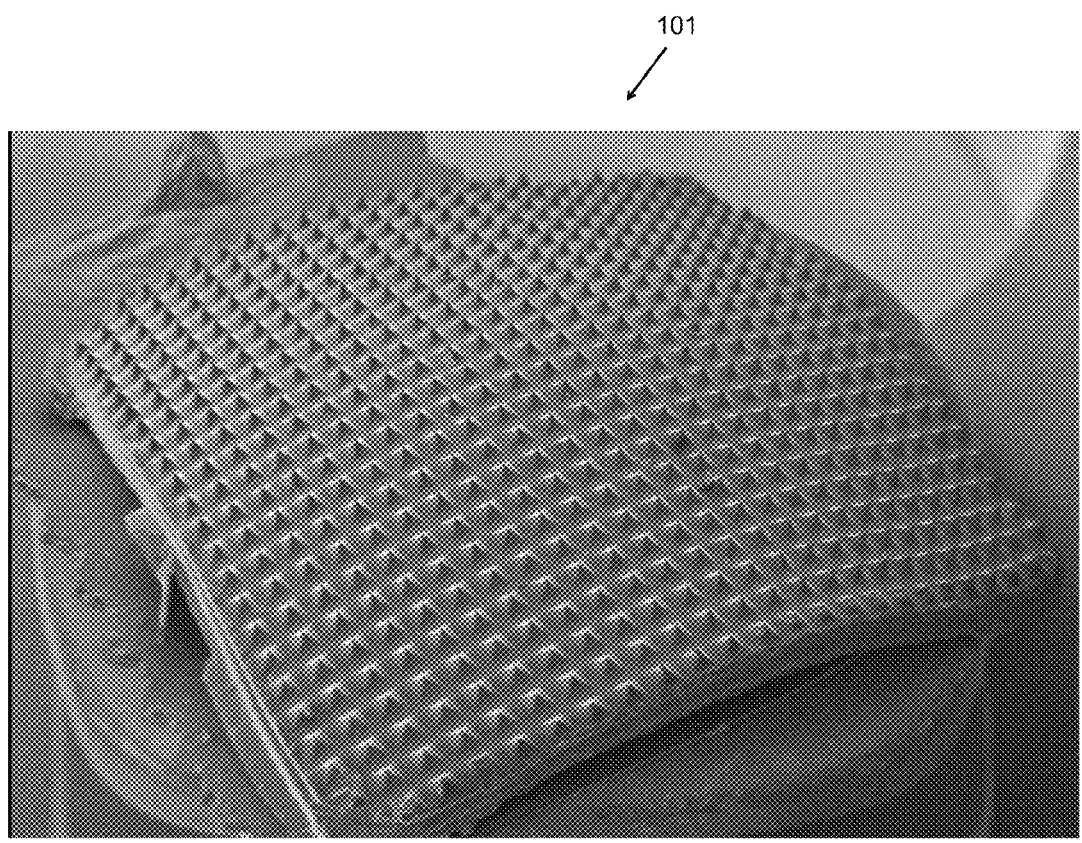
FIG. 11 is a micrograph of another embodiment of a microarray which is in a domed configuration.
Figure 12A:
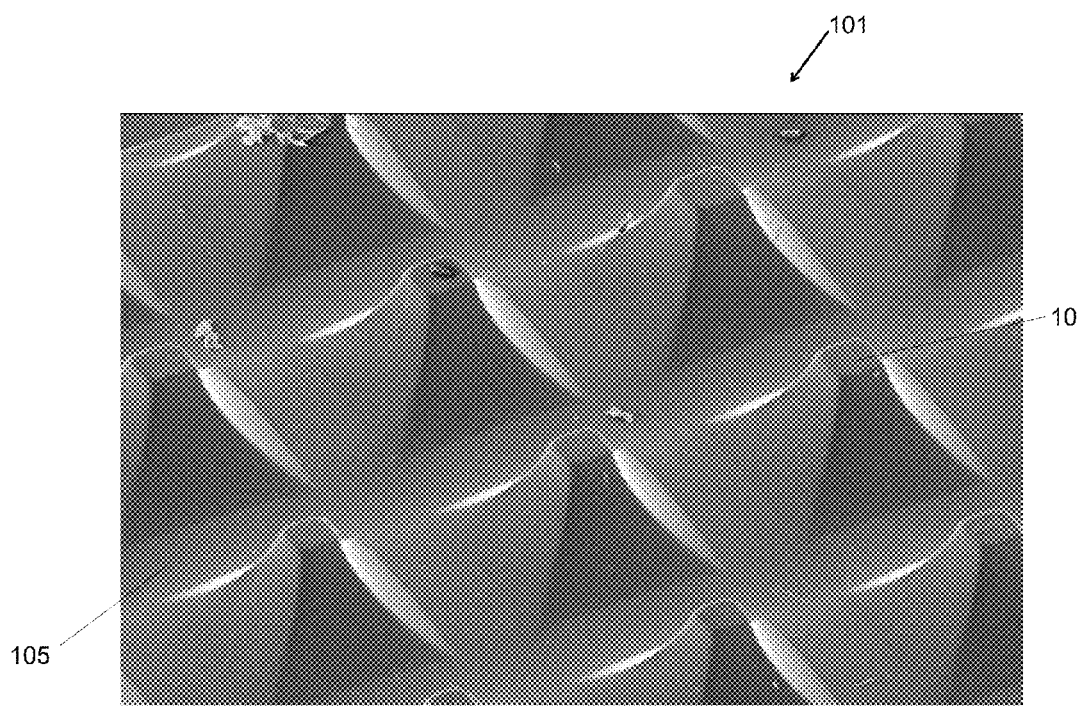
FIG. 12A is a micrograph of the embodiment of FIG. 11, prior to the doming operation.
Figure 12B:
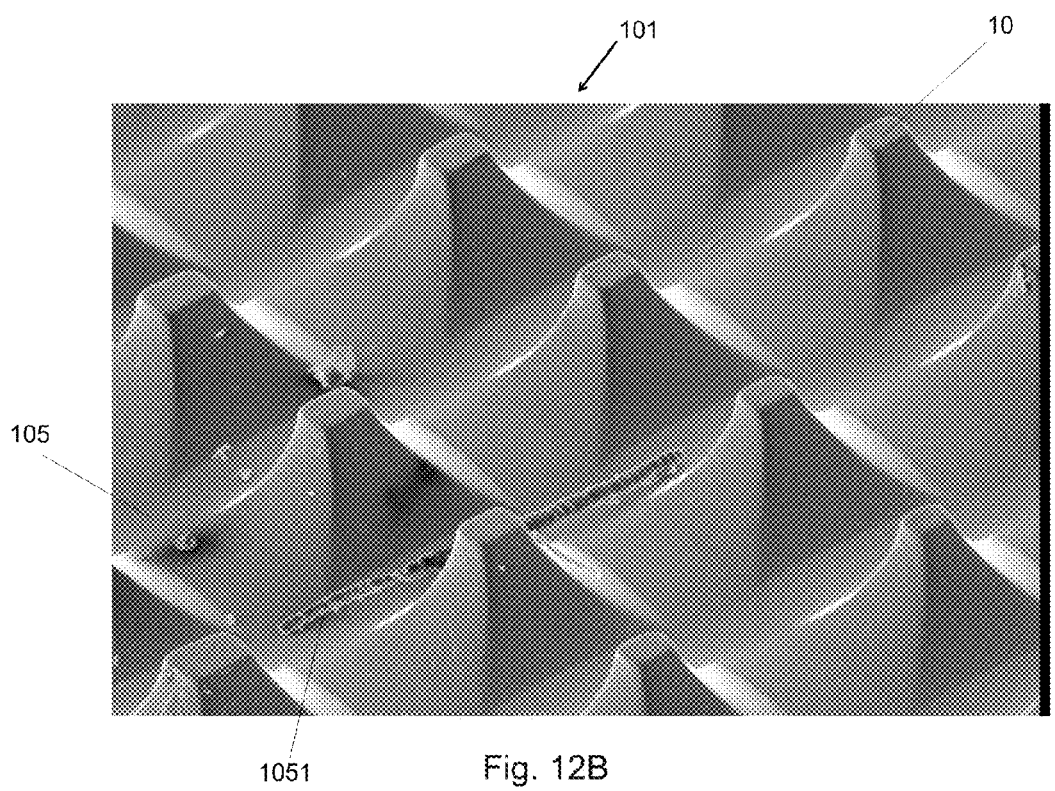
FIG. 12B is a micrograph detail view of the embodiment of FIG. 11.

FIG. 11, is a micrograph of a platen formed in a lenticular fashion. The microprotrusion array 101 is formed such that a substantially planar array of earlier embodiments is formed into a lenticular-type microprotrusion array. The forming is such that there is no degradation of microprotrusions as evidenced by FIGS. 12A and 12B. FIG. 12A shows a substantially planar microprotrusion array 101 which has been formed into a lenticular microprotrusion array of FIG. 12B. FIG. 12B demonstrates that unexpectedly there is no degradation of the shape and form of the microprotrusions 10, and there is no degradation of the platen surface 105. Object 1051 in the micrograph is foreign matter and not related to the operation of the invention.

A process outlined to create the microprotrusion array 101 of FIG. 11 is as follows: A split fixture with a top and bottom block is utilized to hold the microprotrusion array of FIG. 12A. A substantially planar microprotrusion array 101 is fixedly placed in the bottom block, with the microprotrusions 10 facing down. A forming mandrel in the top block is lowered onto the microprotrusion array 101, after uniformly heating microprotrusion array 101 to a temperature such that microprotrusion array 101 may be plastically deformed. After the top block is lowered onto the bottom block and reaches a stopping point, microprotrusion array 101 is plastically formed to the shape of the forming mandrel. The next step is cooling microprotrusion array 101 to such a temperature that the geometry of the forming mandrel is substantially maintained, which is preferably a lenticular shape. As can be seen in FIG. 11, the process creates a slight doming of the part, which currently varies from approximately 0.040" to 0.10 inches in total height from the center of microprotrusion array 101 to the edge of microprotrusion array 101. Although the process outlined is representative of a process for forming a shaped microprotrusion array, it is not the only process and one skilled in the art may alter the order and parameters of the process to achieve substantially the same result, which is a formed microprotrusion array with minimal damage to the peaks and platen surface.

Figure 13:
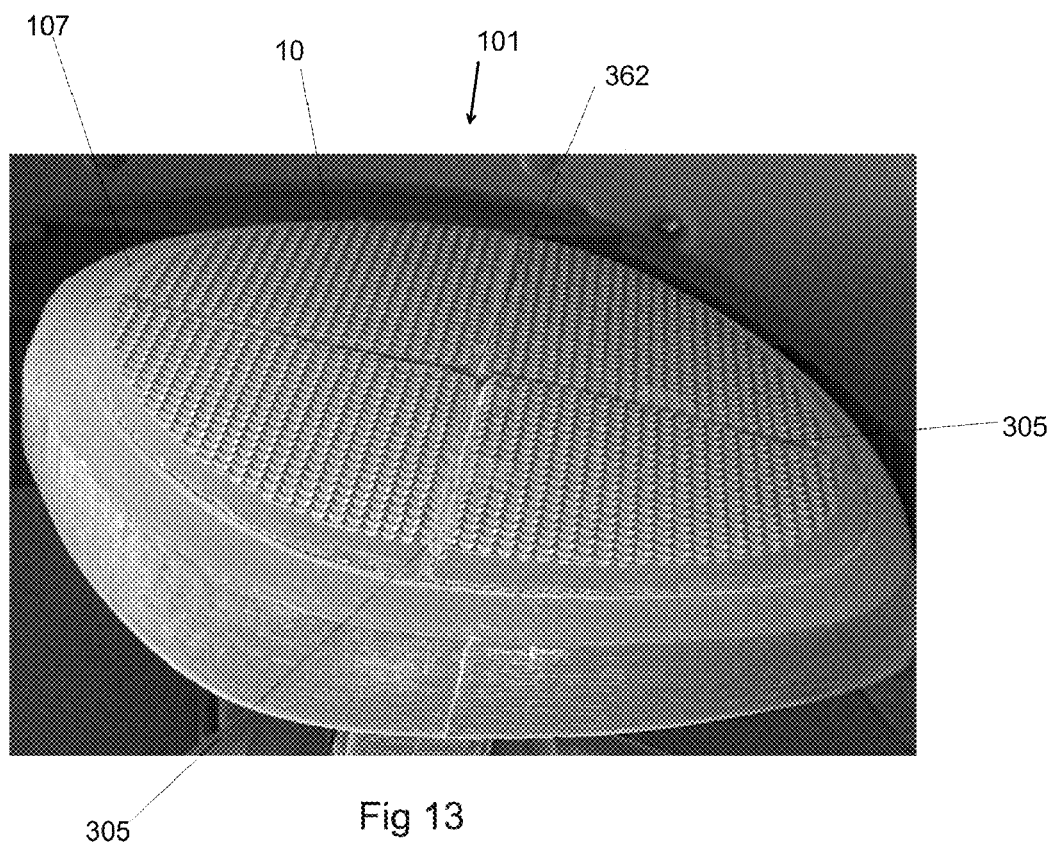
FIG. 13 is a micrograph of another embodiment of the invention which contains micro-channels for the drug to flow during delivery.

FIG. 13 shows another embodiment of the instant invention in which the microchannels 305 have been designed for enhanced fluidic communication of the drug reservoir to the full surface of the platen 102. Drug orifice 362 is in fluidic communication to a drug reservoir and is approximately 0.008 inches in diameter. In addition to lacking microprotrusions 10, microchannels 305 have been optionally recessed into platen 102 to increase fluid conduction properties of microchannels 305. Microchannel 305 is approximately 0.011 inches in width and extends radially from orifice 362. Orifice 362 is in fluid communication to a drug reservoir, and is simultaneously in communication to microchannels 305. Alternatively, a multiple platen design may be utilized to create the microchannels.

Beside the shapes and configurations of the microarrays the materials from or of which the various features are made plan a role in how well the arrays perform their task of abrading and resisting fluid displacement. If a material is hydrophobic, and the substance being administered is water based then this material property will tend to counteract the design characteristics of the array and the array could displace more fluid that if the array was made with a more hydroscopic material. Of course material treatments may be employed to alter the materials properties and make them more, or less, hydrophobic as needed.

While several embodiments have been shown to illustrate the present invention, it will be understood by those skilled in the art that various changes and modifications can be made without departing from the scope of the invention as defined in the appended claims.

What is claimed is:

1. A method for forming a lenticular micro protrusion array comprising:
   providing a substantially planar microprotrusion array comprising a plurality of microprotrusions each protrusion comprising a frustoconical protrusion with at least one scraping edge attached to a planar substrate;
   providing a fixture having a top block and a bottom block wherein the fixture is adapted to hold the planar microprotrusion array, and the top block further comprises a lenticular forming mandrel adapted to deform the planar microprotrusion array;

removably affixing the planar microprotrusion array into the bottom block with the plurality of microprotrusions facing away from the top block;

heating the microprotrusion array to a temperature such that microprotrusion array may be plastically deformed;

lowering the forming mandrel onto the microprotrusion array;

cooling the microprotrusion array to such a temperature that the geometry of the forming mandrel is substantially maintained.

2. The method of claim 1 further comprising deforming the planar array approximately 0.040" to 0.10 inches in total height from the center of microprotrusion array to an edge of microprotrusion array.

3. The method of claim 1, wherein the plurality of microprotrusions are substantially unchanged in shape.

4. The method of claim 1, wherein the lenticular microprotrusion array has areas of differing microprotrusion densities.

5. The method of claim 1 wherein said microprotrusion array is comprised of a thermoplastic material.

6. The method of claim 1 wherein the lenticular microprotrusion array is a substantially a converging meniscus.

7. The method of claim 1 wherein the lenticular microprotrusion array is a substantially a diverging meniscus.

8. The method of claim 1 wherein the lenticular microprotrusion array is a substantially a cylindrical bend.

* * * * *